United States Patent [19]

Borgardt

[11] Patent Number: 4,821,671
[45] Date of Patent: Apr. 18, 1989

[54] CAPTIVE VOLUME DEVICE AS A SAFE LIFE MONITOR

[75] Inventor: Frank G. Borgardt, Cupertino, Calif.

[73] Assignee: The United States of America as represented by the Secretary of the Air Force, Washington, D.C.

[21] Appl. No.: 749,335

[22] Filed: Jun. 27, 1985

[51] Int. Cl.⁴ .................................... G01L 19/12
[52] U.S. Cl. ........................ 116/270; 116/DIG. 8; 116/206
[58] Field of Search ............... 116/206, DIG. 41, 266, 116/270, 200, 201, 268, 272, DIG. 8; 422/56, 58, 59, 86; 436/2, 106, 117, 118, 169

[56] References Cited

U.S. PATENT DOCUMENTS

| | | | |
|---|---|---|---|
| 2,040,798 | 5/1936 | Schoonmaker | 116/200 |
| 2,213,765 | 9/1940 | Iddings | 116/200 |
| 2,417,449 | 3/1947 | Rubin | 116/DIG. 8 |
| 2,960,389 | 11/1960 | Zihlman | 422/56 |
| 2,963,351 | 12/1960 | Stanford et al. | 422/117 |
| 3,111,930 | 11/1963 | Zipper | 116/DIG. 8 |
| 3,217,689 | 11/1965 | Knight et al. | 116/206 |
| 3,388,075 | 6/1968 | Brauer | 436/118 |
| 3,455,655 | 7/1969 | Plantz et al. | 422/86 |
| 3,467,601 | 9/1969 | Brauer | 252/408 |
| 3,507,623 | 4/1970 | McConnaughey | 422/86 |
| 3,547,069 | 12/1970 | Tao | 116/70 |
| 3,574,552 | 4/1971 | Rakowski | 436/117 |
| 3,620,677 | 11/1971 | Morison | 116/200 |
| 3,681,027 | 8/1972 | Smith | 422/117 |
| 4,031,847 | 6/1977 | Sullivan | 116/65 |
| 4,166,429 | 9/1979 | Smorzaniuk | 116/202 |
| 4,408,557 | 10/1983 | Bradley et al. | 116/206 |

FOREIGN PATENT DOCUMENTS 413821 6/1910 France .............................. 116/206

Primary Examiner—William A. Cuchlinski, Jr.
Assistant Examiner—W. Morris Worth
Attorney, Agent, or Firm—William Stepanishen; Donald J. Singer

[57] ABSTRACT

A captive volume device containing a small amount of solid propellant and a safe life indicator such as a colorimeter material or a differential pressure sensor. As the propellant deteriorates, it expends a gas which changes the color of the colorimeter material or causes the differential pressure sensor to alter its position, indicating that the propellant material is useless.

3 Claims, 1 Drawing Sheet

CAPTIVE VOLUME DEVICE AS A SAFE LIFE MONITOR

STATEMENT OF GOVERNMENT INTEREST

The invention described herein may be manufactured and used by or for the Government for governmental purposes without the payment of any royalty thereon.

BACKGROUND OF THE INVENTION

The present invention relates broadly to a safe life monitor apparatus, and in particular to a captive volume device to monitor the safe life of an expendible material.

In the prior art, previous attempts to develop an apparatus such as a safe life monitor for propellant material have been based upon methods which directly sense a change in the propellant material in the propulsion device, i.e. a rocket motor, etc. The problems which exist with the prior art methods and apparatus, is the unreliable methods and means that are utilized to directly measure the small changes in the gassing rates, the mechanical and/or physical properties of expendible material over long periods of time. This type of monitoring and measuring of an expendible material is difficult to do reliably and is affected by the changes in ambient and operating temperature and pressure.

One method of determining and sensing the presence of various gases which is well known and widely accepted involves passing a sample of the gas through an elongate transparent tube in which there is contained a colorimetric indicator. The colorimetric indicator reacts to the presence of the gas sample by changing the color of the colorimeter material in the transparent tube. In order to provide a quantitative measure of the detected gas, the reaction of the colorimeter material to a particular gas sample may be preset to achieve a specific color or develop a particular color stain length. In general, it is required that colorimeter indicator tubes be sealed for storage and, when they are to be used for gas detection and analysis, a portion of the tube will be removed to expose the gas to the colorimeter material.

One of the gases that is useful to detect, is nitrogen oxide. In determining nitrogen oxides, it is common to utilize a granular carrier base with a coating of tetraphenylbenzidine or dimethyldiphenylbenzidine to operate as the indicator. Some prior art indicators have utilized a diphenylbenzidinedecasulfonic acid or a water soluble salt of diphenylbenzidinedecasulfonic acid that is carried by a granular solid. The granular solid carrier which may preferably be a granular absorbent, does not enter into the color-producing reaction. The granular carrier provides an inert physical carrier base for the reagent material. Silica gel is the preferred carrier among the various carriers which are available. However, any water soluble salt of diphenylbenzidine-decasulfonic acid may be used. It may be noted that certain alkali metal salts, such as sodium salts, are generally preferred.

While such indicators as described above are very sensitive to nitrogen oxides in general, they have the distinct disadvantage of very rapidly deteriorating with exposure to oxygen. Thus, these colorimeter materials require very careful handling and any presence of oxygen must be removed from the tubes prior to filling. The preparation of such colorimeter indicators requires great care. For Example, the benzidine component and the granular carrier must be heated to sublime the benzidine component into the carrier and unless this operation is carefully performed, it may result in an uneven distribution of reagent on the support material.

On such useful device or technique which is used as a means of measuring and or monitoring the end of the useful life of materials, such as solid rocket propellants, is the present captive volume device. The captive volume device may comprise a small parasitic unit which is attached to the structure that contains the material whose lifetime is to be monitored. Various types of propellant measuring and or monitoring devices are shown to exist in the prior art.

In the prior art, it may be seen that a colorimetric $NO_x$ detector has been utilized for a propellant, but not in a captive volume device. It may be further seen that colorimetric $NO_x$ detectors are well known and have been used to evaluate mediums other than propellants.

The use of a passive differential pressure sensing device is well known in the prior art. Some such differential pressure sensing devices are the use of snap action diaphragms, reverse buckling diaphragms, rupture disks, reverse buckling rupture disks, belleville springs and bellows. One such prior art device discloses a pressure ratio reversal indicator which includes a sight glass and a reversible diaphragm, although the device is not identified as a captive volume device apparatus. A similar device discloses a fluid pressure indicator which utilizes a diaphragm and sight glass arrangement. The present invention involves a captive volume device to measure the useful life of a solid propellant. This device utilizes a colorimetric $NO_x$ detector contained in a small volume of the captive volume device along with a sample of the propellant. With the nitrate ester stabilizer concentration being adjusted to a lower level than that of the main propellant, the propellant in the captive volume device will reach its gassing point prior to the main batch. The onset of gassing indicates that the end of safe life has been reached in the case of this type of propellant.

SUMMARY OF THE INVENTION

The present invention utilizes a closed chamber or structure to enclose a small of amount of a solid propellant whose useful life is to be measured or sensed. The closed chamber forms a captive volume device in which there is included a detecting means. The useful life detecting means may comprise either colorimetric material which change color or a differential pressure device which changes its position in relationship to the useful life of the solid propellant material. A visual viewing port is provided in the captive volume device to allow the state of the detecting means to be observed.

It is one object of the present invention, therefore, to provide an improved captive volume apparatus.

It is another object of the invention to provide an improved captive volume apparatus as a safe life monitor for a solid propellant material.

It is another object of the invention to provide an improved captive volume apparatus in which an active useful life sensor device is utilized to measure the safe life of the propellant.

It is another object of the invention to provide an improved captive volume apparatus in which a passive useful life sensor device is utilized to measure the safe life of the propellant.

These and other advantages, objects and features of the invention will become more apparent after considering the following description taken in conjunction with

DESCRIPTION OF THE PREFERRED EMBODIMENT

Figure 1:
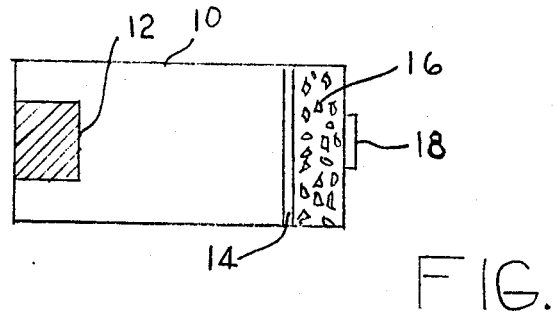
FIG. 1 is a schematic diagram of the captive volume device in a colorimeter configuration, and, FIGS. 2a and 2b are schematic diagrams, respectively, of the captive volume device in a differential pressure configuration in which the safe/replace diaphram positions are respectively illustrated.

Referring now to FIG. 1, there is shown a schematic diagram of a captive volume device as a safe life monitor which is arranged in a colorimeter detector configuration. The captive volume device comprises a closed chamber or structure 10 in which there is positioned at one end a sample of material 12, such as a solid rocket propellant. The material sample 12 comprises some expendible type of material which has a useful life that may be either variable or undetermined. The useful life of the sample material 12 may also be temperature dependent.

At the opposite end of the structure 10, there is positioned a screen 14 which functions as both a separator and to form a compartment for a colorimeter detector material 16. The colorimeter detector material 16 comprises a granular absorbent carrier such as silica gel or other suitable material which is coated with any of a number reagents that react to produce a particular color or a color change. At the colorimeter detector end of the structure 10 there is provided a view port 18 which is arranged such a manner that the color or color change of the colorimeter detector material may be easily observed.

The captive volume device is a means of measuring/monitoring the end of useful life of materials such as solid rocket propellants. The apparatus, as shown in FIG. 1, utilizes the captive volume structure as the enclosing means in which a small parasitic unit is formed to maintain the detector material in close chemical proximity to the material whose life time is to be monitored. This is to insure that the expended gassing concentration from the test material in the main structure experiences the same time/temperature history as the detector material.

The captive volume apparatus comprises a small closed (no more than a few cubic inches) container or structure which is adaptable to a variety of geometries that maybe required by any specific application. Within the captive volume apparatus is located a small amount of the material whose useful life is to be monitored and a means of detecting the time at which end of safe life is reached. The detector means may comprise a physical, mechanical or chemical change indicator which can be readily monitored by casual inspection at selected time intervals. Depending upon the particular mechanism by which the material of interest ages, there is the possibility to adjust concentrations of selected ingredients such that the material sample within the captive volume apparatus will reach the end of its useful life at a known interval of time ahead of the major material. This accelerated time interval will then provide a reference time frame in which the major material or unit must be replaced with another fresh unit, thus allowing for logistics without a major time lapse during which the equipment would be unavailable for reliable use.

The captive volume apparatus was directed at the specific problem which occurs with solid propellant rocket motor fuels that are stored for extended time periods prior to use. The captive volume apparatus provides the method and means to monitor the aging of rocket motor solid propellant materials to the point of usefulness. Thus, an accurate, reliable, inexpensive, and passive (if necessary or required) detector means which would indicate when the propellant reaches the end of its safe useful life was needed. While the basic structure and mode of operation of the captive volume apparatus has been described above with respect to a specific embodiment, it should be noted that several methods to detect and signal the end of the safe useful life of propellants are possible and may be utilized.

For example, in the case of a solid propellants which utilize nitrate esters, the captive volume apparatus would use a colormetric $NO_x$ detector that is contained in one end of the small volume of the captive volume apparatus along with a sample of the propellant at the other end. The nitrate ester stabilizer concentration maybe adjusted to a lower level than that of the main propellant concentration. Thus, the propellant in the captive volume apparatus will reach its gassing point at a time prior to the main propellant material. The onset of gassing indicates that the end of the safe life for this type of solid propellant has been reached. This operational time differential will allow a sufficient time period in which the propellant fuel in a main rocket motor may be retrieved and replaced. In FIG. 1, there is shown a captive volume apparatus which is structured to accomplish the above purpose.

Figure 2A:
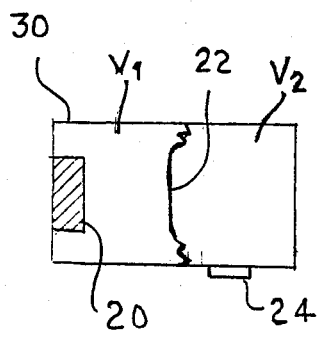
Figure 2B:
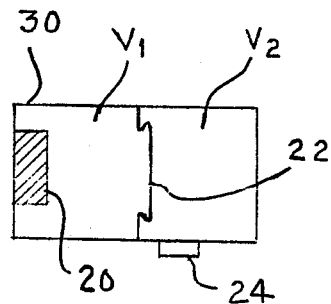

Turning now to FIGS. 2a, 2b there is shown a captive volume apparatus which utilizes a passive pressure sensing device to monitor and detect the end of safe life for a propellant material that utilizes nitrate esters. The captive volume apparatus of FIGS. 2a, 2b comprises the same basic structure as shown in FIG. 1 except that the safe life detecting means that is utilized comprises a differential pressure sensing diaphram 22. As in FIG. 1, the propellant material 20 is contained in one end of the structure 30. In FIG. 2a, the diaphram position indicator/sensor means 22 is shown in the safe use position. In this configuration, the captive volume apparatus utilizes the gas pressure which will build-up as the propellent material reaches the point of depletion of its stabilizer, to flip the folded or corregated diaphragm 22 to the inverted position. In FIG. 2b, the diaphram 22 is shown in inverted or replace (propellant useful life expended) position. This event can be viewed thru the view point 24 by utilizing any of a number of obvious optical methods. The free volumes $V_1$ and $V_2$ are adjusted to be equal in the safe position. This approach will allow the captive volume device detector to operate at a variety of temperature and pressure cyclic conditions without falsely triggering the diaphragm 22 to flip. Several approaches for the diaphragm design are possible depending upon the pressure differential which is selected or required to flip the diaphram and the readout system that is utilized. Some of these approaches include: snap action diaphragms, reverse buckling diaphragms, rupture disks, reverse buckling rupture disks, belleville springs and bellows.

Although the invention has been described with reference to a particular embodiment, it will be understood to those skilled in the art that the invention is capable of a variety of alternative embodiments within the spirit and scope of the appended claims.

What is claimed is:

1. A captive volume apparatus for use as a safe life monitor comprising in combination:

a means for enclosing a volume, said volume enclosing means having a first and second end, said volume enclosing means containing at said first end thereof an expendable material, a means for detecting gas, said detecting means being contained within said second end of said volume enclosing means, said detecting means monitoring a state of said expendable material, said detecting means providing a visual indication when said expendable material has reached the end of its useful life, said detecting means comprises a differential pressure sensing means, and, a means for viewing, said viewing means being mounted on said second end of said volume enclosing means to provide viewing access to said visible indication of said detecting means.

2. A captive volume apparatus as described in claim 1 wherein said pressure differential sensing means comprises a diaphragm position indicator/sensor, said diaphragm position indicator/sensor having a first and second position indication.

3. A captive volume apparatus as described in claim 2 wherein said first position indication represents the safe use position and said second position indication represents the safe life end position.

* * * * *